US008765173B2

(12) United States Patent
Aleksov et al.

(10) Patent No.: US 8,765,173 B2
(45) Date of Patent: Jul. 1, 2014

(54) DRUG DELIVERY SYSTEM FOR ADMINISTRATION OF A WATER SOLUBLE, CATIONIC AND AMPHIPHILIC PHARMACEUTICALLY ACTIVE SUBSTANCE

(75) Inventors: Julian Aleksov, Lidingö (SE); Igor Lokot, Uppsala (SE)

(73) Assignee: Ardenia Investments, Ltd., London, Greater London (GB)

( * ) Notice: Subject to any disclaimer, the term of this patent is extended or adjusted under 35 U.S.C. 154(b) by 0 days.

(21) Appl. No.: 12/809,259

(22) PCT Filed: Dec. 18, 2008

(86) PCT No.: PCT/SE2008/051516
§ 371 (c)(1),
(2), (4) Date: Sep. 15, 2010

(87) PCT Pub. No.: WO2009/078803
PCT Pub. Date: Jun. 25, 2009

(65) Prior Publication Data
US 2011/0123607 A1 May 26, 2011

(30) Foreign Application Priority Data
Dec. 19, 2007 (WO) .................. PCT/SE2007/001129

(51) Int. Cl.
*A61K 9/48* (2006.01)
(52) U.S. Cl.
USPC ........... 424/452; 424/465; 424/489; 514/785; 514/34; 514/283; 514/654; 977/773; 977/788; 977/906
(58) Field of Classification Search
CPC ... A61K 47/4803; A61K 9/0019; A61K 9/10; A61K 9/145; A61K 9/5123
See application file for complete search history.

(56) References Cited

U.S. PATENT DOCUMENTS

| 6,197,809 B1 | 3/2001 | Strelchenok | |
|---|---|---|---|
| 2004/0048923 A1* | 3/2004 | Strelchenok et al. | 514/553 |
| 2005/0191359 A1* | 9/2005 | Goldshtein et al. | 424/489 |
| 2007/0082838 A1 | 4/2007 | De et al. | |

FOREIGN PATENT DOCUMENTS

| EP | 1 666 031 A1 | 6/2006 |
|---|---|---|
| WO | 01/17546 | 3/2001 |
| WO | 02/092600 | 11/2002 |
| WO | 2005/089106 | 9/2005 |
| WO | 2006/017246 A2 | 2/2006 |
| WO | 2006/106519 | 10/2006 |
| WO | 2007/001356 | 1/2007 |
| WO | 2009/078802 | 6/2009 |
| WO | 2009/078804 | 6/2009 |

OTHER PUBLICATIONS doxorubicin-official monograph; p. 606, left column; www.sinoapi.com/Pharmacopoeia/jp15/JP25316-40-9.pdf.*
chemical book; www.chemicalbook.com. May 24, 2012.*
Saadia Hassan et al., "Cytotoxic activity of a new paclitaxel formulation, Pacliex, in vitro and in vivo", Cancer Chemother Pharmacol, 2005, vol. 55, pp. 47-54.
D. V. Arsenov et al., "Synthesis of N-(all-transretinoyl)doxorubicin and study of the antitumor activity of its complex with blood serum proteins", Pharmaceutical Chemistry Journal, 2001, vol. 35, No. 4, pp. 186-189.
Mahesh Chavanpatil et al., "Polymer-Surfactant Nanoparticles for Sustained Release of Water-Soluble Drugs", Journal of Pharmaceutical Sciences, Dec. 2007, vol. 96, No. 12 pp. 3379-3389.
International Search Report for corresponding International Application No. PCT/SE2008/051516 mailed Mar. 20, 2009.
Written Opinion for corresponding International Application No. PCT/SE2008/051516 mailed Mar. 20, 2009.
Written Opinion of the International Preliminary Examining Authority for corresponding International Application No. PCT/SE2008/051516 mailed Nov. 20, 2009.
International Preliminary Report on Patentability for corresponding International Application No. PCT/SE2008/051516 mailed Mar. 25, 2010.
International Search Report for corresponding International Application No. PCT/SE2008/051515 mailed Mar. 20, 2009.
Written Opinion for corresponding International Application No. PCT/SE2008/051515 mailed Mar. 20, 2009.
Written Opinion of the International Preliminary Examining Authority for corresponding International Application No. PCT/SE2008/051515 mailed Nov. 20, 2009.
International Preliminary Report on Patentability for corresponding International Application No. PCT/SE2008/051515 mailed Oct. 19, 2009.
International Search Report for corresponding International Application No. PCT/SE2008/051517 mailed Mar. 20, 2009.
Written Opinion for corresponding International Application No. PCT/SE2008/051517 mailed Mar. 20, 2009.
PCT Communication in Cases for Which No Other Form Is Suitable—Corrected International Search Report and Written Opinion for corresponding International Application No. PCT/SE2008/051517 mailed Apr. 1, 2009.
Written Opinion of the International Preliminary Examining Authority for corresponding International Application No. PCT/SE2008/051517 mailed Nov. 20, 2009.
International Preliminary Report on Patentability for corresponding International Application No. PCT/SE2008/051517 mailed Mar. 25, 2010.

(Continued)

*Primary Examiner* — Suzanne Ziska
(74) *Attorney, Agent, or Firm* — Renner, Otto, Boisselle & Sklar, LLP

(57) ABSTRACT

A drug delivery system (DDS) for administration of a water soluble, cationic, and amphiphilic pharmaceutically active substance (API) which DDS comprises poorly water soluble nanoparticles formed by the API together with a Na-salt of N-all-trans-retinoyl cysteic acid methyl ester and/or a Na-salt of N-13-cis-retinoyl cysteic acid methyl ester. A pharmaceutical composition comprising such a DDS. Methods for preparation of such a DDS and such a pharmaceutical composition. Use of such a DDS and pharmaceutical composition for treatment of cancer.

22 Claims, 3 Drawing Sheets

(56) References Cited

OTHER PUBLICATIONS

Saadia Hassan et al., "Cytotoxic activity of a new paclitaxel formulation, Pacliex, in vitor and in vivo", Cancer Chemother Pharmaacol, 2005, vol. 55, pp. 47-54.

Torchilin, "Micellar Nanocarriers: Pharmaceutical Perspectives", Pharmaceutical Research, vol. 24, No. 1, Jan. 2007, pp. 1-16.
Office Action issued Jun. 25, 2013 in the corresponding Japanese Patent Application No. 2010-539386.

* cited by examiner

DRUG DELIVERY SYSTEM FOR ADMINISTRATION OF A WATER SOLUBLE, CATIONIC AND AMPHIPHILIC PHARMACEUTICALLY ACTIVE SUBSTANCE

FIELD OF THE INVENTION

This application is a national phase of International Application No. PCT/SE2008/051516 filed Dec. 18, 2008 and published in the English language, which claims priority to International Application No. PCT/SE2007/001129 filed Dec. 19, 2007.

This invention relates to a drug delivery system for administration of amphiphilic cationic pharmaceutically active substances, a pharmaceutical composition comprising such a drug delivery system, and a method for the preparation of such a drug delivery system. The invention also relates to the use of such a drug delivery system for the preparation of a medicament for the treatment of cancer.

Furthermore the invention also relates to a method for enhancing the drug efficiency of amphiphilic pharmaceutically active substances, and to a method for increasing the bioavailability of amphiphilic pharmaceutically active substances.

BACKGROUND

Two important parameters related to the efficaciousness of drugs are the "therapeutic index" (also known as the "therapeutic ratio") and the "therapeutic window". The therapeutic index is a comparison of the amount of a therapeutic agent that causes the therapeutic effect to the amount that causes toxic effects. Quantitatively, it is the ratio given by the dose required to produce the toxic effect divided by the therapeutic dose. A commonly used measure of therapeutic index $LD_{50}$ divided by $ED_{50}$. The therapeutic window is a parameter for estimation of drug dosage which can treat disease effectively while staying within the safety range. It is the range between the $ED_{50}$ and the starting point of $LD_{50}$ curve. It is believed that adjustment of this parameter can help to avoid most of the potential side effects.

Pharmaceuticals with narrow therapeutic windows are common and are frequent in groups such as, for instance, antiarrhythmics, anticonvulsants, cardiac glycosides, aminoglycosides, cytotoxics, and immunosuppressants.

A large majority of antitumor agents have a very narrow therapeutic window. One way of improving the therapeutic index of such agents is to use suitable infusion regimens. Ideally, the drug concentration is maintained inside the therapeutical window for a desired time range, after which it quickly leaves the body. Prolonged infusions have in general showed god efficacy with few side effects. For instance prolonged infusion is the most efficient way to reduce cardiotoxicity of doxorubicin, one of the mostly used anticancer drugs. However, prolonged infusions (sometimes up to 72 hours) are expensive and inconvenient. Accordingly, great efforts have been made to mimic such infusions by the use of drug delivery systems which can ensure slow release of the active ingredient from various kinds of drug depots. Drug delivery systems comprising such depots are usually provided by way of encapsulation of drugs into nanoparticle of various polymers, polymerosomes, liposomes, or microemulsions.

However, in order to protect itself against hostile intruders of different kind (such as viruses, bacteria and fungal spores) human and animal bodies have developed mechanisms to remove or disintegrate particles larger than about 50 nm. The Reticulo-Endothelial System (RES), a part of the immune system, is the most effective destructor of such particles. The probability for a particle to be targeted by RES increases dramatically with increasing particle size.

Many drugs are provided in a cationic amphiphilic form, such as for instance drugs that have one or more amino groups in their structure. In acid environment these drug substances are transformed into salts, e.g. hydrochlorides, sulphates, lactates or tartrates, and exist predominantly in a protonated form. These transformations increase the solubility of the drugs in aqueous solutions and make it possible to use these solutions for i.v. infusions. After infusion the environment is switched to slightly basic as pH of blood is approximately 7.4, which results in deprotonation of the drugs. This in turn reduces the solubility of the substances, which improves the PK/PD properties of the drug by increasing the grade of protein binding, accelerating penetration of the substances into cells as well as decreasing renal clearance. A lot of antineoplastic drugs are provided in a cationic amphiphilic form, and the described way of administration is applied for drugs as, for instance, doxorubicin and its analogues (epirubicin, daunorubicin, idarubicin), vinca alkaloids (vinblastine, vincristine, vinorelbine), amsacrine, mitoxantrone, topotecan and irinotecan.

US 2004048923 describes a group of retinoids including among numerous others the sodium salt of N-(all-trans-retinoyl)-L-cysteic acid methyl ester and the sodium salt of N-(13-cis-retinoyl)-L-cysteic acid methyl ester. It is stated that the substances make it possible to manufacture new micelle formulations of poorly soluble pharmaceutical compounds like paclitaxel and docetaxel. The teaching of US 2004048923 does not aim for the provision of formation of smaller nanoparticles with decreased water solubility and improved encapsulation capacity.

SHORT SUMMARY OF THE INVENTION

It would be desirable to be able to create a drug delivery system for administration of water soluble amphiphilic cationic pharmaceutically active substances which system would provide for formation of smaller nanoparticles with decreased water solubility and improved encapsulation capacity. This would give better PK/PD properties and improve the therapeutic indexes of the administered drug.

One object of the present invention is to provide such a drug delivery system.

Thus, one aspect of the invention relates to a drug delivery system for administration of a pharmaceutically active substance that is a cationic amphiphile by itself and has a solubility per se in water of at least 4 mg/ml, which drug delivery system comprises nanoparticles having solubility in water below 0.1 mg/ml, said nanoparticles being formed by said substance in association with a sodium salt of the methyl ester of N-all-trans-retinoyl cysteic acid, a sodium salt of methyl ester of N-13-cis-retinoyl cysteic acid, or a combination thereof.

The inventive drug delivery system provides for nanoparticles smaller than about 50 nm and an encapsulation capacity of the methyl ester excipient (expressed as the ratio of the weight of the excipient to the weight of encapsulated drug) of about 1.2.

BRIEF DESCRIPTION OF THE DRAWINGS

The present invention will be described in closer detail in the following description, examples and attached drawings, in which.

DESCRIPTION OF EMBODIMENTS OF THE INVENTION

Figure 1:
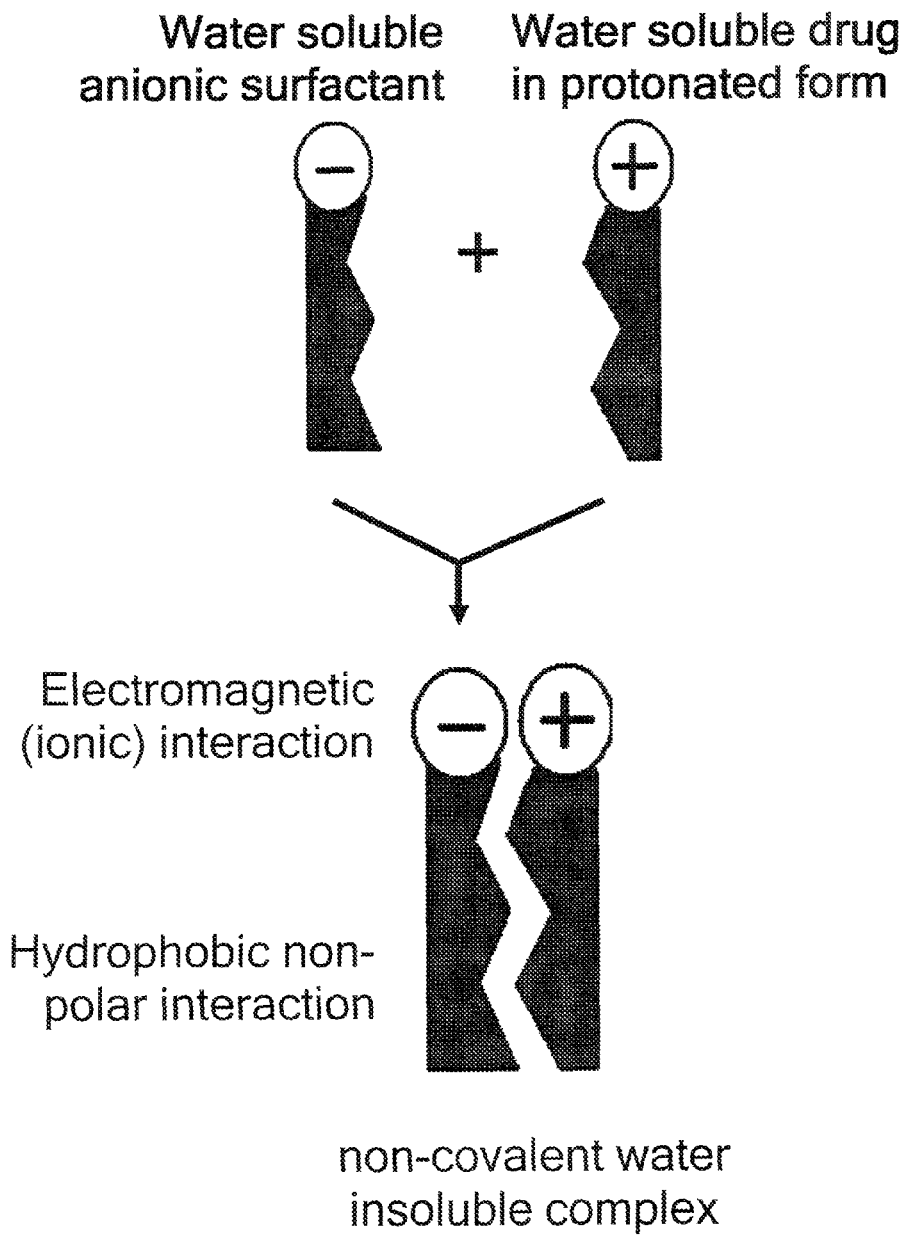
FIG. 1 is a scheme showing the formation of essentially water insoluble nanoparticles by association of cationic amphiphile with a sodium salt of the methyl ester of N-all-trans-retinoyl cysteic acid, a sodium salt of methyl ester of N-13-cis-retinoyl cysteic acid, or a combination thereof.

Before the present invention is disclosed and described, it is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

It must be noted that, as used in this specification and the claims, the singular forms "a", "an", and "the" include plural referents unless the context clearly dictates otherwise.

In this specification, unless otherwise stated, the term "about" modifying the quantity of an ingredient in the drug delivery systems or compositions of the invention or employed in the methods of the invention refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the drug delivery systems or compositions or carry out the methods; and the like. The term "about" also encompasses amounts that differ due to different equilibrium conditions for a composition resulting from a particular initial mixture. Whether or not modified by the term "about", the claims include equivalents to the quantities.

In this specification, unless otherwise stated, the term "pharmaceutically acceptable carrier," means a non-toxic, inert solid, semi-solid or liquid filler, diluent, encapsulating material or formulation auxiliary of any type.

In this specification, unless otherwise stated, the term "drug delivery system" refers to a formulation or device that delivers therapeutic agent(s) to desired body location(s) and/or provides timely release of therapeutic agent(s).

In this specification, unless otherwise stated, the term "pharmaceutically active substance" encompasses any substance that will produce a therapeutically beneficial pharmacological response when administered to a host, including both humans and animals.

In this specification, unless otherwise stated, the term "particle size" refers to the Z-average diameter as measured by dynamic light scattering with the use of red laser with a wavelength of 633 nm.

In this specification, unless otherwise stated, the term "nanoparticle" refers to a microscopic particle whose size is measured in nanometers.

In this specification, unless otherwise stated, the term "solubility" of a substance refers to the ability of that substance to be dissolved in a specified solvent at about room temperature, by which is meant from between about 15° C. to about 38° C.

In this specification, unless otherwise stated, the term "cytotoxic compound" refers to a compound that has the ability of arresting the growth of, or killing, cells.

In this specification, unless otherwise stated, the term "cytostatic compound" refers to a compound that has the ability of bringing cells, although not necessarily lysed or killed, into a permanent non-proliferative state.

In this specification, unless otherwise stated, the term "derivative" refers to a compound formed from the original structure either directly, by a chemical reaction of the original structure, or by a "modification" which is a partial substitution of the original structure, or by design and de novo synthesis. Derivatives may be synthetic, or may be metabolic products of a cell or an in vitro enzymatic reaction.

In one embodiment the nanoparticles of the inventive drug delivery system have solubility in water below 0.01 mg/ml.

In another embodiment the pharmaceutically active substance is non-covalently associated with the sodium salt of the methyl ester of N-all-trans-retinoyl cysteic acid, the sodium salt of methyl ester of N-13-cis-retinoyl cysteic acid, or a combination thereof.

The cationic pharmaceutically active substance may, for instance, have one or more amino groups; the counter-anion may, for instance, be chloride, sulphate, lactate, or tartrate. The substance may be of natural, synthetic, or semi-synthetic origin.

In one embodiment the pharmaceutically active substance is a cytotoxic or a cytostatic compound; in one aspect of this embodiment the cytotoxic or cytostatic compound is a protonated form of doxorubicin, mitoxantrone, epirubicin, daunorubicin, idarubicin, topotecan, irinotecan, vinblastine, vincristine, vinorelbine, amsacrine, procarbazine, mechlorethamine, or a combination thereof; in a specific aspect said compound is a protonated form of doxorubicin; in another aspect said compound is a protonated form of mitoxantrone.

According to other embodiments of the present invention there is also provided:
- the use of the inventive drug delivery system for the preparation of a medicament for the treatment of cancer, and to a method for the treatment of cancer wherein the inventive drug delivery system is administered in a therapeutically effective amount to a patient in need of such treatment; and
- the use of the inventive pharmaceutical composition for the preparation of a medicament for the treatment of cancer, and to a method for the treatment of cancer, wherein the inventive pharmaceutical composition is administered in a therapeutically effective amount to a patient in need of such treatment.

Another embodiment of the invention relates to a pharmaceutical composition comprising a pharmaceutically acceptable carrier and a drug delivery system of this kind. In one aspect of this embodiment the pharmaceutically active substance is a cytotoxic or a cytostatic compound; in one aspect of this embodiment the pharmaceutical composition may be provided in the form of an aqueous solution, a gel, a cream, an ointment, a tablet, a capsule, or a softgel.

Such a composition may be prepared by, for instance, mixing an aqueous solution of a pharmaceutically active substance which comprises one or more protonated amino group(s), e.g. a hydrochloride, sulphate, lactate, or tartrate, with more than one equivalent of sodium salt of the methyl ester of N-all-trans-retinoyl cysteic acid, sodium salt of methyl ester of N-13-cis-retinoyl cysteic acid, or combination thereof, per amino group. This is illustrated by the below formula, showing a hydrochloride example:

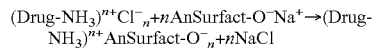

in which
the term "AnSurfact-O$^-$" denotes an anion of methyl ester of N-all-trans-retinoyl cysteic acid, or methyl ester of N-13-cis-retinoyl cysteic acid, or combination thereof; and
the term "(Drug-NH$_3$)$^{n+}$" denotes a pharmaceutically active substance with protonated amino group(s)

As seen, n equivalent(s) of AnSurfact-O$^-$ binds to (Drug-NH$_3$)$^{n+}$ forming an essentially water insoluble complex according to the formula, and the rest amount of AnSurfact-O$^-$ is applied for ensuring the solubility of the complex obtained.

The excess of AnSurfact-O$^-$ can be in the range of 0.2-10 equivalents. Pure water or different aqueous solutions can be used as a solvent in this process. These novel composition obtained by mixing of ammonium salts of the drug with AnSurfact-O$^-$ can be used directly or freeze dried for further use.

A further embodiment of the invention relates to the use of a sodium salt of the methyl ester of N-all-trans-retinoyl cysteic acid, a sodium salt of the methyl ester of N-13-cis-retinoyl cysteic acid, or a combination thereof, in the preparation of such a drug delivery system.

A further embodiment of the invention relates to the use of a sodium salt of the methyl ester of N-all-trans-retinoyl cysteic acid, a sodium salt of the methyl ester of N-13-cis-retinoyl cysteic acid, or a combination thereof, for hydrophobation of a cationic amphiphilic substance which has a solubility per se in water of at least 4 mg/ml; in one aspect of this embodiment said cationic amphiphilic substance is a cytotoxic or a cytostatic compound.

Another embodiment of the invention relates to a method for the preparation of a drug delivery system for administration of at least one pharmaceutically active substance that is a cationic amphiphile by itself and has a solubility per se in water of at least 4 mg/ml, wherein said substance is combined with a sodium salt of the methyl ester of N-all-trans-retinoyl cysteic acid, a sodium salt of methyl ester of N-13-cis-retinoyl cysteic acid, or a combination thereof to form nanoparticles having a solubility in water below 0.1 mg/ml; in one aspect of this embodiment said sodium salt of the methyl ester of N-all-trans-retinoyl cysteic acid, sodium salt of methyl ester of N-13-cis-retinoyl cysteic acid, or combination thereof is non-covalently bound to said substance. In a further aspect of this embodiment the substance is combined with an excess of about 0.2-10 equivalents of said sodium salt of the methyl ester of N-all-trans-retinoyl cysteic acid, sodium salt of methyl ester of N-13-cis-retinoyl cysteic acid, or combination thereof. In a specific embodiment of the embodiment the nanoparticles have solubility in water below 0.01 mg/ml.

In one aspect of this embodiment the sodium salt of the methyl ester of N-all-trans-retinoyl cysteic acid, sodium salt of methyl ester of N-13-cis-retinoyl cysteic acid, or combination thereof is mixed in a mol/mol ratio of 1:1 with a hydrochloride, sulphate, lactate, or tartrate of doxorubicin or analogue thereof, such as epirubicin, daunorubicin, or idarubicin; topotecan; irinotecan; or amsacrine to provide nanoparticles that are essentially non-soluble in water.

In a case of pharmaceutically active substances with more than one amino groups, such as for instance mitoxantrone and vinca alkaloids, the amount of methyl ester of N-all-trans-retinoyl cysteic acid, sodium salt of methyl ester of N-13-cis-retinoyl cysteic acid, or combination thereof should correspond to the number of protonated amino groups.

Another embodiment of the invention relates to a method for the preparation of pharmaceutical composition comprising a pharmaceutically acceptable carrier and a drug delivery system according to any one of claims 1-8, wherein said drug delivery system is combined with an amount of about 0.2-10 equivalents, based on the cationic charge of the amphiphile comprised in the drug delivery system, of the methyl ester of N-all-trans-retinoyl cysteic acid, a sodium salt of methyl ester of N-13-cis-retinoyl cysteic acid, or a combination thereof.

Another embodiment of the invention relates to a method for enhancing the drug efficiency of at least one pharmaceutically active substance that is a cationic amphiphile by itself and has a solubility per se in water of at least 4 mg/ml, wherein said substance is combined with a sodium salt of the methyl ester of N-all-trans-retinoyl cysteic acid, a sodium salt of methyl ester of N-13-cis-retinoyl cysteic acid, or a combination thereof to form nanoparticles having a solubility in water below 0.1 mg/ml; in one aspect of this embodiment said sodium salt of the methyl ester of N-all-trans-retinoyl cysteic acid, sodium salt of methyl ester of N-13-cis-retinoyl cysteic acid, or combination thereof is non-covalently bound to said substance.

In a further aspect of this embodiment said substance is combined with an excess of about 0.2-10 equivalents of said sodium salt of the methyl ester of N-all-trans-retinoyl cysteic acid, sodium salt of methyl ester of N-13-cis-retinoyl cysteic acid, or combination thereof. In a specific embodiment of the embodiment the nanoparticles have solubility in water below 0.01 mg/ml.

Another embodiment of the invention relates to a method for increasing the bioavailability of at least one pharmaceutically active substance that is a cationic amphiphile by itself and has solubility per se in water of at least 4 mg/ml, wherein said substance is combined with a sodium salt of the methyl ester of N-all-trans-retinoyl cysteic acid, a sodium salt of methyl ester of N-13-cis-retinoyl cysteic acid, or a combination thereof to form nanoparticles having a solubility in water below 0.1 mg/ml; in one aspect of this embodiment the sodium salt of the methyl ester of N-all-trans-retinoyl cysteic acid, sodium salt of methyl ester of N-13-cis-retinoyl cysteic acid, or combination thereof is non-covalently bound to said substance. In a further aspect of this embodiment said substance is combined with an excess of about 0.2-10 equivalents of said sodium salt of the methyl ester of N-all-trans-retinoyl cysteic acid, sodium salt of methyl ester of N-13-cis-retinoyl cysteic acid, or combination thereof. In a specific embodiment of the embodiment the nanoparticles have solubility in water below 0.01 mg/ml.

The nanoparticles of the inventive drug delivery system provide for lower polarity and decreased water solubility, which in turn lead to improved cell membrane penetration and stronger binding to proteins, leading to increased potency.

The invention will be illustrated in closer detail in the following non-limiting examples.

EXAMPLES

Materials and Methods

The formulations used were either freshly prepared or obtained by reconstitution of freeze dried pharmaceutically active substances with a sodium salt of the methyl ester of N-all-trans-retinoyl cysteic acid, a sodium salt of the methyl ester of N-13-cis-retinoyl cysteic acid, or a combination thereof, by a specified solution for reconstitution.

Doxorubicin was purchased from Mercian Corporation, Japan. Mitoxantrone, Topotecan and Irinotecan were purchased from Chemtronica KB, Sweden. Adriamycin and Doxil were purchased from pharmacy stores and reconstituted according to manufacturers prescribing information.

The particle size of the formulations was measured by dynamic light scattering method with the use of a red laser (633 nm, Nano-ZS, Malvern Instruments Ltd). Average values of three independent measurements were calculated for plotting of particle size. Y-error bars are composed by +/− standard deviation of the measurements.

For evaluation of cytotoxicity in vitro cells of different human tumour cell lines were purchased from American Type Culture Collection (Rockville, Md., USA): Human Breast Adenocarcinoma Cell Line MDA-MB-231 (ATCC-HTB-26, Lot 3576799), Human Ovary Adenocarcinoma Cell Line SKOV-3 (ATCC-HTB-77, Lot 3038337) and Human Lung Non-Small Cancer Cell Line A549 (ATCC-CCL-185, Lot 3244171). MDA-MB-231 cells were propagated in MEM culture medium with 2 mM L-glutamine, 10% fetal bovine serum (FBS) and antibiotics. SKOV-3 cells were cultured in McCoy's 5A culture medium, supplemented with 1.5 mM L-glutamine, 10% FBS and antibiotics. All media and supplements were purchased from Sigma-Aldrich Co. (St. Louis, Mo., USA). Cell propagation of all lines was carried out in BD Falcon™ 25 or 75 cm² cultivation flasks (Becton Dickinson Labware). A549 cells were cultured in Ham's F-12 culture medium with 1 mM L-glutamine, 10% FBS and antibiotics. Cell propagation of all lines was carried out in BD Falcon™ 25 or 75 cm² cultivation flasks.

Drug cytotoxicity testing was carried out using BD Falcon™ 96-well cultivation plates for adherent cells (Becton Dickinson Labware). These plates were seeded by cells at $8\times10^3$ cells/well for MDA-MB-231, at $10\times10^3$ cells/well for SKOV-3 or at $6\times10^3$ cells/well for A549 in a volume of 200 μl/well. Both flasks and cultivation plates were incubated for cell growth at 37° C. in a humidified atmosphere of 95% air and 5% $CO_2$.

The cell cultures in the cultivation plates were allowed to adhere for 24 hour of incubation. On day 1 after cell seeding 4 μL solutions of the formulations to be tested with different concentrations in appropriate solvents were added to wells with cultures (dose-response experiments). In the control cultures 4 μL of the solvents were added as solvent control. The cells were incubated within 2-4 consecutive days. At the end of the incubation period adherent cells were detached by trypsinization and the number of viable cells was counted using trypan blue exclusion test and a hemocytometer. All experiment were performed at least tree times and data were derived from an average of three determinations each in four replicates. The results were expressed as mean cell number±SE and the differences between control and test series evaluated by means of Student's t-test. The drug cytotoxicity was evaluated based on the extent of cell growth inhibition. The cell growth inhibition by the tested drugs was calculated as follows:

$$\text{Cell growth inhibition \%} = \frac{\text{Control} - \text{Test Series}}{\text{Control}} \times 100$$

In control series 4 μL of different solvents used for drug testing were added to cultures as negative solvent controls. The differences between these control series were insignificant; therefore an average of negative controls was applied for calculations.

Solutions of generic compounds like doxorubicin hydrochloride, mitoxantrone dihydrochloride, topotecan hydrochloride etc., as well as their commercial formulations were used as positive controls. The differences in growth inhibition by these drugs in different solvents were insignificant; therefore an average inhibition of positive controls was applied for calculations.

The mean $IC_{50}\pm SE$ was calculated on the basis of at least three separate experiments.

Enhancement factors (EF) were calculated by dividing $IC_{50}$ of the control comparison drug with $IC_{50}$ of the inventive formulation.

Example 1

Transformation of Doxorubicin Hydrochloride into Deprotonated Form 20 mg doxorubicin hydrochloride (0.034 mmol), which is soluble in water in an amount of more than 25 mg/ml, was dissolved in 10 ml of water. 3.4 ml of sodium hydroxide (0.01 M) was added to the solution while stirring. During the mixing a fine precipitation emerged. The precipitate was separated by centrifugation of the test tube at 3000 rpm for 10 min. The supernatant was removed and the precipitate was shaken with 10 ml of water followed by a new centrifugation. After three additional washing procedures as described above the supernatant was filtered through a 0.2 mm filter in order to remove possible large aggregates of the product. The solubility of doxorubicin in amine form was measured by UV method at wavelength 495 nm and was equal to 0.015 mg/ml.

Example 2

Transformation of Mitoxantrone Dihydrochloride into Deprotonated Form 26 mg mitoxantrone dihydrochloride (0.05 mmol) was dissolved in 10 ml of water. 10 ml sodium hydroxide (0.01 M) was added to the solution while stirring. During the mixing a fine precipitation emerged. The precipitate was separated by centrifugation of the test tube at 3000 rpm for 10 min. The supernatant was removed and the precipitate was shaken with 10 ml of water followed by a new centrifugation. After three additional washing procedures as described above the supernatant was filtered through 0.2 mm filter in order to remove possible large aggregates of the product. The solubility of mitoxantrone in amine form was measured by UV method at wavelength 660 nm and was equal to 0.03 mg/ml.

Example 3

Transformation of Topotecan Hydrochloride into Deprotonated Form 23 mg topotecan hydrochloride (0.05 mmol) was dissolved in 10 ml of water. 5 ml sodium hydroxide (0.01 M) was added to the solution while stirring. During the mixing a fine precipitation emerged. The precipitate was separated by centrifugation of the test tube at 3000 rpm for 10 min. The supernatant was removed and the precipitate was shaken with 10 ml of water followed by a new centrifugation. After three additional washing procedures as described above the supernatant was filtered through 0.2 mm filter in order to remove possible large aggregates of the product. The solubility of topotecan in amine form was measured by UV method at wavelength 385 nm and was equal to 0.09 mg/ml.

Example 4

Formation of Particles Consisting of Doxorubicin in Protonated Form and Methyl Ester of N-all-trans-retinoyl Cysteic Acid in Deprotonated Form Aqueous solutions of sodium salt of methyl ester of N-all-trans-retinoyl cysteic acid (2 ml, 5 mg/mL) and doxorubicin hydrochloride (6 ml, 2 mg/ml) were mixed in a 10 ml test tube. During the mixing a fine precipitation emerged. The precipitate was separated by centrifugation of the test tube at 3000 rpm for 10 min. The supernatant was removed and the precipitate was shaken with 10 ml of water followed by a new centrifugation. After three additional washing procedures as described above the supernatant was filtered through 0.2 mm filter in order to remove possible large aggregates of the product. The solubility of the obtained particles was measured by UV method at wavelength 350 nm and was equal to 0.0002 mg/ml.

Example 5

Formation of Particles Consisting of Mitoxantrone in Diprotonated Form and Two Equivalents of Methyl Ester of N-all-trans-retinoyl Cysteic Acid in Deprotonated Form Aqueous solutions of sodium salt of methyl ester of N-all-trans-retinoyl cysteic acid (2 ml, 5 mg/mL) and mitoxantrone dihydrochloride (5.2 ml, 1 mg/ml) were mixed in a 10 ml test tube. During the mixing a fine precipitation emerged. The precipitate was separated by centrifugation of the test tube at 3000 rpm for 10 min. The supernatant was removed and the precipitate was shaken with 10 ml of water followed by a new centrifugation. After three additional washing procedures as described above the supernatant was filtered through 0.2 mm filter in order to remove possible large aggregates of the product. The solubility of the obtained particles was measured by UV method at wavelength 660 nm and was equal to 0.002 mg/ml.

Example 6

Formation of Particles Consisting of Topotecan in Protonated Form and Methyl Ester of N-all-trans-retinoyl Cysteic Acid in Deprotonated Form Aqueous solutions of sodium salt of methyl ester of N-all-trans-retinoyl cysteic acid (2 ml, 5 mg/mL) and topotecan hydrochloride (4.7 ml, 2 mg/ml) were mixed in a 10 ml test tube. During the mixing a fine precipitation emerged. The precipitate was separated by centrifugation of the test tube at 3000 rpm for 10 min. The supernatant was removed and the precipitate was shaken with 10 ml of water followed by a new centrifugation. After three additional washing procedures as described above the supernatant was filtered through 0.2 mm filter in order to remove possible large aggregates of the product. The solubility of the obtained particles was measured by UV method at wavelength 364 nm and was equal to 0.024 mg/ml.

Example 7

Preparation of a Formulation of Doxorubicin with Sodium Salt of Methyl Ester of N-all-trans-retinoyl Cysteic Acid and Sodium Salt of Methyl Ester of 13-cis-retinoyl Cysteic Acid 50 ml doxorubicin hydrochloride solution (8.6 mg/ml) was added drop-wise under stirring to 200 ml of a solution containing sodium salt of methyl ester of N-all-trans-retinoyl cysteic acid (3 mg/mL) and sodium salt of methyl ester of 13-cis-retinoyl cysteic acid (3 mg/ml) in 500 ml round-bottom flask. Stirring was continued for an additional 20 min. The doxorubicin concentration in the obtained formulation was 1.6 mg/ml. The solution obtained was filtered through 0.2 mm filter and freeze dried. The filtration did not result in reduction of doxorubicin concentration.

Example 8

Preparation of a Formulation of Topotecan with Sodium Salt of Methyl Ester of N-all-trans-retinoyl Cysteic Acid Methanol stock-solutions of topotecan hydrochloride (120 ml, 1.09 mg/ml) and sodium salt of methyl ester of N-all-trans-retinoyl cysteic acid (32 ml, 15 mg/ml) were mixed in a 500 ml round-bottom flask and evaporated in vacuo. 120 ml sodium chloride solution (9 mg/ml) was added to the residue obtained after evaporation, and the mixture was stirred until it became clear and transparent (approx. 20 min). The concentration of topotecan in the obtained solution was 1 mg/ml, corresponding to a topotecan hydrochloride concentration of 1.09 mg/ml. The solution obtained was filtered through 0.2 mm filter. The filtration did not result in reduction of topotecan concentration.

Example 9

Preparation of a Formulation of Irinotecan with Sodium Salt of Methyl Ester of N-all-trans-retinoyl Cysteic Acid Methanol stock-solutions of irinotecan hydrochloride trihydrate (100 ml, 1.15 mg/ml) and sodium salt of methyl ester of N-all-trans-retinoyl cysteic acid (27 ml, 15 mg/ml) were mixed in a 500 ml round-bottom flask and evaporated in vacuo. 100 ml of water was added to the residue obtained after evaporation and the mixture was stirred until it became clear and transparent (approx. 30 min). The concentration of irinotecan in the obtained solution was 1 mg/ml, corresponding to an irinotecan hydrochloride trihydrate concentration of 1.15 mg/ml. The obtained solution was filtered through 0.2 mm filter and freeze dried. The filtration did not result in reduction of irinotecan concentration.

Example 10

Investigation of the Dependence of Particle Size Formed by Sodium Salt of Methyl Ester of N-13-cis-retinoyl Cysteic Acid and Doxorubicin Hydrochloride (w/w Ratio 2.3:1) on the Concentration of Doxorubicin Solutions were prepared by reconstitution of freeze dried samples consisted of the mixture of sodium salt of methyl ester of N-13-cis-retinoyl cysteic acid and doxorubicin with w/w ratio 2.3:1 in aqueous solution containing (130 mmol), $CaCl_2$ (2 mmol) and $MgCl_2$ (0.8 mmol).

TABLE 1

| Concentration of doxorubicin, mg/ml | Average particle size, nm | St. dev. |
|---|---|---|
| 0.004 | 31.7 | 1.2 |
| 0.1 | 31.3 | 1.7 |
| 0.3 | 40.7 | 1.2 |
| 1 | 55.7 | 1.7 |
| 3 | 69.0 | 4.3 |

Figure 2:
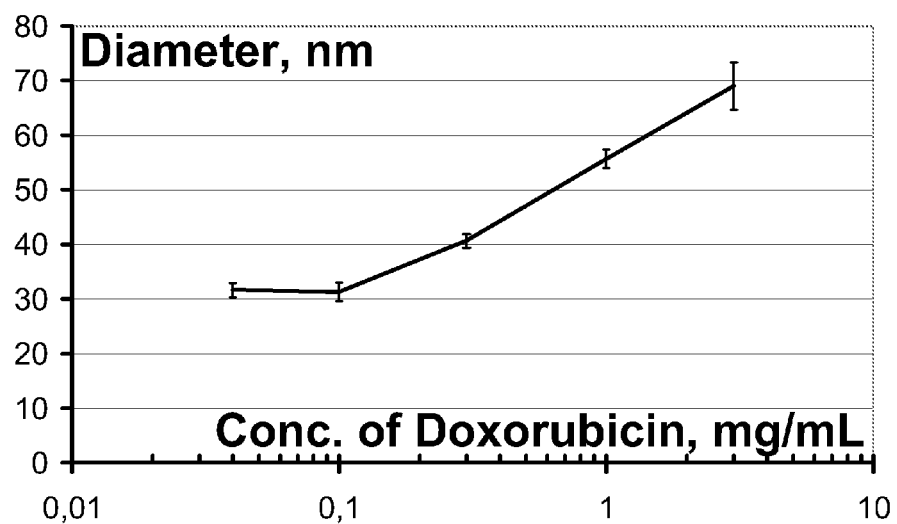
FIG. 2 shows the dependence of the size of the particles formed by sodium salt of methyl ester of N-13-cis-retinoyl cysteic acid and doxorubicin hydrochloride (w/w ratio 2.3:1) on the concentration of doxorubicin. Solvent: aqueous solution of NaCl (130 mmol), $CaCl_2$ (2 mmol) and $MgCl_2$ (0.8 mmol).

As shown in Table 1 and FIG. 2 a decrease of concentration results in a decrease of particle size in a range of concentrations 0.1-3 mg/ml. Further dilution does not influence on the particle size.

Example 11

Investigation of the Kinetics of Dissolving of Particles

A starting solution was prepared by dissolving a freeze dried sample of a mixture of sodium salt of methyl ester of N-all-trans-retinoyl cysteic acid and doxorubicin hydrochloride in w/w ratio 2.1:1 in an aqueous solution of NaCl (5.9 mg/mL), KCl (0.3 mg/mL), $CaCl_2$ (0.295 mg/mL), $MgCl_2$ hexahydrate (0.2 mg/mL) and sodium acetate (4.1 mg/mL) to a doxorubicin concentration of 2 mg/ml. The starting solution was diluted 50 times to a doxorubicin concentration of 0.04 mg/ml, the obtained solution was vigorously stirred on the vortex for 10 seconds and used directly for measurements of average particle size.

TABLE 2

| Time after dilution, min | Average particle size, nm | St. dev. |
|---|---|---|
| 1.5 | 61.1 | 5.9 |
| 2 | 50.0 | 3.3 |
| 3 | 42.7 | 2.6 |
| 7 | 40.3 | 3.3 |
| 20 | 40.7 | 2.5 |
| 60 | 34.6 | 2.1 |
| 120 | 31.3 | 0.9 |
| 300 | 30.9 | 1.6 |

Figure 3:
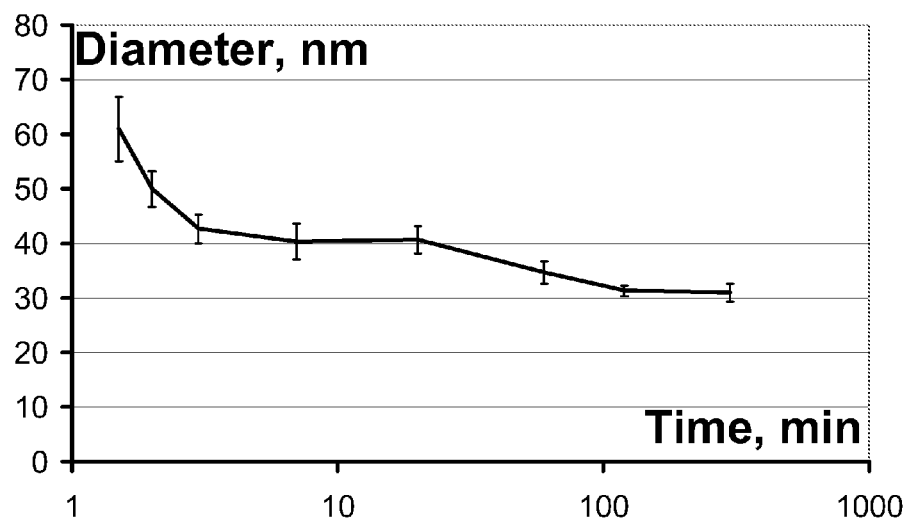
FIG. 3 shows the kinetics of dissolving particles after dilution of a formulation of sodium salt of methyl ester of N-all-trans-retinoyl cysteic acid and doxorubicin hydrochloride in w/w ratio 2.1:1. Solvent: aqueous solution of NaCl (5.9 mg/mL), KCl (0.3 mg/mL), $CaCl_2$ (0.295 mg/mL), $MgCl_2$ hexahydrate (0.2 mg/mL), Sodium acetate (4.1 mg/mL). Dilution from 2 to 0.04 mg/mL doxorubicin.
Figure 4:
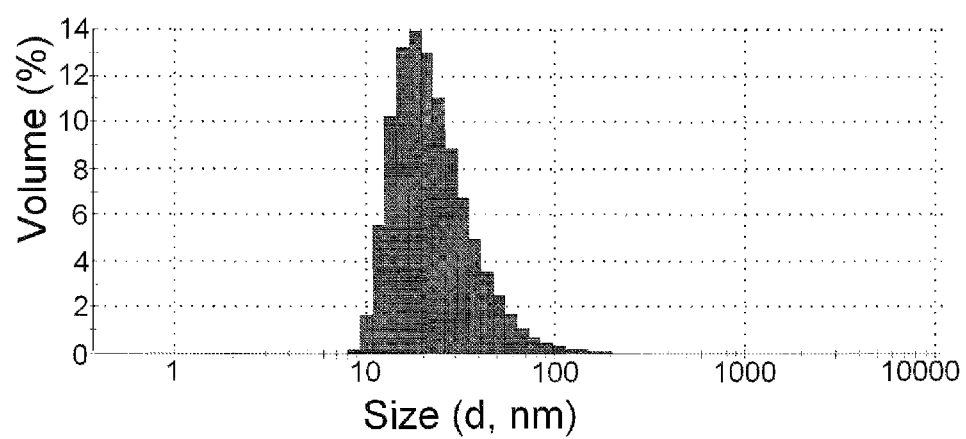
FIG. 4 shows the size distribution by volume of formulation obtained by reconstitution of freeze-dried mixture of doxorubicin, sodium salt of methyl ester of N-all-trans-retinoyl cysteic acid and sodium salt of methyl ester of N-13-cis-retinoyl cysteic acid (w/w/w 1:1.05:1.05) in solution of NaCl (9 mg/mL), doxorubicin concentration 0.5 mg/ml.

As shown in Table 2 and FIG. 3 the rate of decreasing of particle size is slowed down with time until almost insoluble particles are formed.

Biological Evaluation

Examples 12-15

In vitro experiments on different malignant cell culture lines like breast adenocarcinoma, ovary adenocarcinoma and lung non-small cell cancer showed that the activity of formulations of cationic amphiphilic compounds depends dramatically on the nature of counter ions as well as morphology of nanoparticles. The use of the methyl ester of N-all-trans-retinoyl cysteic acid, the methyl ester of N-13-cis-retinoyl cysteic acid, or combinations thereof reduces the solubility of the cationic amphiphilic compounds, which facilitates the transport of the compounds through cell membrane resulting in increased potency of such formulations.

The following commercial formulations were used as references in the below Examples: DOXIL® (doxorubicin hydrochloride formulated into pegylated liposomes), NOVANTRONE® (mitoxantrone hydrochloride), ADRIAMYCIN® (doxorubicin hydrochloride), HYCAMTIN® (topotecan hydrochloride), and CAMPTO® (irinotecan hydrochloride)

Example 12

Comparative Evaluation of Cytotoxicity of the Formulations in Cultures of Human Breast Adenocarcinoma MDA-MB-231 Cell Line Formulations containing mixtures of nanoparticles of the methyl ester of N-all-trans-retinoyl cysteic acid and the methyl ester of N-13-cis-retinoyl cysteic acid were prepared by dissolving freeze dried powder in appropriate aqueous solutions. Dilutions of commercial formulations were made according to instructions of the manufacturers. The results are set forth in Table 3 below.

TABLE 3

| Formulation | Solvent | Particle size, nm | $IC_{50}$ day 3 | EF day 3 | $IC_{50}$ day 4 | EF day 4 |
|---|---|---|---|---|---|---|
| ADRIAMYCIN® | 9 mg/ml NaCl | — | $(1.9 \pm 0.13) \times 10^{-7}$ | — | $(5.1 \pm 0.17) \times 10^{-8}$ | — |
| DOXIL® | 50 mg/ml glucose | 100 | $(2.3 \pm 0.15) \times 10^{-6}$ | $0.08^a$ | $(2.8 \pm 0.10) \times 10^{-7}$ | $0.18^a$ |
| Doxorubicin-Na salt of methyl ester of N-all-trans-retinoyl cysteic acid-Na salt of methyl ester of N-13-cis-retinoyl cysteic acid 1:1.1:1.1 (w/w/w) | 9 mg/ml NaCl | 34 | $(2.0 \pm 0.17) \times 10^{-8}$ | $9.5^a$ | $(1.4 \pm 0.07) \times 10^{-8}$ | $3.6^a$ |
| NOVANTRONE® | 50 mg/ml glucose | — | $(7.5 \pm 0.38) \times 10^{-8}$ | — | $(5.1 \pm 0.21) \times 10^{-9}$ | — |
| Mitoxantrone-Na salt of methyl ester of N-all-trans-retinoyl cysteic acid-Na salt of methyl ester of N-13- | 50 mg/ml glucose | — | $(8.1 \pm 0.29) \times 10^{-9}$ | $9.3^b$ | $(2.0 \pm 0.12) \times 10^{-9}$ | $2.6^b$ |

TABLE 3-continued

| Formulation | Solvent | Particle size, nm | IC$_{50}$ day 3 | EF day 3 | IC$_{50}$ day 4 | EF day 4 |
|---|---|---|---|---|---|---|
| cis-retinoyl cysteic acid 1:3.4:3.4 (w/w/w) | | | | | | |
| HYCAMTIN ® Topotecan-Na salt of methyl ester of N-all-trans-retinoyl cysteic acid-Na salt of methyl ester of N-13-cis-retinoyl cysteic acid 1:3.4:3.4 (w/w/w) | 9 mg/ml NaCl 6 mg/ml NaCl, 0.3 mg/ml KCl, calcium chloride hexahydrate 0.4 mg/ml CaCl$_2$ dihydrate, 3.1 mg/ml Na lactate | — 14 | (9.2 ± 1.4) × 10$^{-7}$ (1.7 ± 0.12) × 10$^{-7}$ | — 5.4$^c$ | (4.4 ± 0.33) × 10$^{-8}$ (1.4 ± 0.19) × 10$^{-8}$ | — 3.1$^c$ |
| CAMPTO ® Irinotecan-Na salt of methyl ester of N-all-trans-retinoyl cysteic acid-Na salt of methyl ester of N-13-cis-retinoyl cysteic acid 1:3.4:3.4 (w/w/w) | 9 mg/ml NaCl 6 mg/ml NaCl, 0.3 mg/ml KCl, calcium chloride hexahydrate 0.4 mg/ml CaCl$_2$ dihydrate, 3.1 mg/ml Na lactate | — 12 | (3.0 ± 0.09) × 10$^{-5}$ (8.1 ± 0.19) × 10$^{-6}$ | — 3.7$^d$ | (3.2 ± 0.10) × 10$^{-6}$ (1.9 ± 0.11) × 10$^{-6}$ | — 1.7$^d$ |

Enhancement factors were calculated versus:
[a]ADRIAMYCIN ®,
[b]NOVANTRONE ®,
[c]HYCAMTIN ® and
[d]CAMPTO ®.

Example 13

Comparative Evaluation of Cytotoxicity of the Formulations in Cultures of Human Ovary Adenocarcinoma SKOV-3 Cell Line Formulations containing mixtures of nanoparticles of the methyl ester of N-all-trans-retinoyl cysteic acid and the methyl ester of N-13-cis-retinoyl cysteic acid were prepared by dissolving of freeze dried powder in appropriate aqueous solutions. Dilutions of commercial formulations were made according to instructions of the manufacturers. The results are set forth in Table 4 below.

TABLE 4

| Formulation | Solvent | Particle size, nm | IC$_{50}$ day 3 | EF day 3 | IC$_{50}$ day4 | EF day 4 |
|---|---|---|---|---|---|---|
| ADRIAMYCIN ® | 9 mg/ml NaCl | — | (8.5 ± 0.27) × 10$^{-8}$ | — | (4.8 ± 0.16) × 10$^{-8}$ | — |
| DOXIL ® | 50 mg/ml glucose | 100 | (4.8 ± 0.18) × 10$^{-6}$ | 0.02$^a$ | (8.0 ± 0.27) × 10$^{-7}$ | 0.06$^a$ |
| Doxorubicin-Na salt of methyl ester of N-all-trans-retinoyl cysteic acid-Na salt of methyl ester of N-13-cis-retinoyl cysteic acid 1:1.1:1.1 (w/w/w) | 9 mg/ml NaCl | 34 | (5.2 ± 0.25) × 10$^{-8}$ | 1.6$^a$ | (2.8 ± 0.1) × 10$^{-8}$ | 1.7$^a$ |
| NOVANTRONE ® | 50 mg/ml glucose | — | (9.6 ± 0.45) × 10$^{-8}$ | — | (1.8 ± 0.32) × 10$^{-9}$ | — |
| Mitoxantrone-Na salt of methyl ester of N-all-trans-retinoyl cysteic acid-Na salt of methyl ester of N-13-cis-retinoyl cysteic acid 1:3.4:3.4 (w/w/w) | 50 mg/ml glucose | — | (2.0 ± 0.09) × 10$^{-9}$ | 4.8$^b$ | (9.2 ± 0.12) × 10$^{-10}$ | 2.0$^b$ |
| HYCAMTIN ® | 9 mg/ml NaCl | — | (3.5 ± 0.42) × 10$^{-5}$ | — | (1.0 ± 0.27) × 10$^{-6}$ | — |
| Topotecan-Na salt of methyl ester of N-all-trans-retinoyl cysteic acid-Na salt of methyl ester of N-13-cis-retinoyl | 6 mg/ml NaCl, 0.3 mg/ml KCl, calcium chloride hexahydrate 0.4 mg/ml | 14 | (5.0 ± 0.22) × 10$^{-7}$ | 70$^c$ | (2.1 ± 0.08) × 10$^{-8}$ | 48$^c$ |

TABLE 4-continued

| Formulation | Solvent | Particle size, nm | IC$_{50}$ day 3 | EF day 3 | IC$_{50}$ day4 | EF day 4 |
|---|---|---|---|---|---|---|
| cysteic acid 1:3.4:3.4 (w/w/w) | CaCl$_2$ dihydrate, 3.1 mg/ml Na lactate | | | | | |
| CAMPTO ® | 9 mg/ml NaCl | — | $(4.2 \pm 0.18) \times 10^{-5}$ | — | $(4.0 \pm 0.19) \times 10^{-5}$ | — |
| Irinotecan-Na salt of methyl ester of N-all-trans-retinoyl cysteic acid-Na salt of methyl ester of N-13-cis-retinoyl cysteic acid 1:3.4:3.4 (w/w/w) | 6 mg/ml NaCl, 0.3 mg/ml KCl, calcium chloride hexahydrate 0.4 mg/ml CaCl$_2$ dihydrate, 3.1 mg/ml Na lactate | 12 | $(1.2 \pm 0.09) \times 10^{-5}$ | 3.5[d] | $(4.2 \pm 0.27) \times 10^{-6}$ | 9.5[d] |

Enhancement factors were calculated versus:
[a]ADRIAMYCIN ®,
[b]NOVANTRONE ®,
[c]HYCAMTIN ® and
[d]CAMPTO ®.

Example 14

Comparative Evaluation of Cytotoxicity of the Formulations in Cultures of Human Lung Non-Small Cancer Cell Line A549

Formulations containing mixtures of nanoparticles of the methyl ester of N-all-trans-retinoyl cysteic acid and the methyl ester of N-13-cis-retinoyl cysteic acid were prepared by dissolving of freeze dried powder in appropriate aqueous solutions. Dilutions of commercial formulations were made according to instructions of the manufacturers. The results are set forth in Table 5 below.

TABLE 5

| Formulation | Solvent | Particle size, nm | IC$_{50}$ day 3 | EF day 3 | IC$_{50}$ day4 | EF day 4 |
|---|---|---|---|---|---|---|
| ADRIAMYCIN ® | 9 mg/ml NaCl | — | $(1.2 \pm 0.09) \times 10^{-8}$ | — | $(2.7 \pm 0.21) \times 10^{-8}$ | — |
| DOXIL ® | 50 mg/ml glucose | 100 | $(1.9 \pm 0.18) \times 10^{-7}$ | 0.06[a] | $(1.4 \pm 0.08) \times 10^{-7}$ | 0.19[a] |
| Doxorubicin-Na salt of methyl ester of N-all-trans-retinoyl cysteic acid-Na salt of methyl ester of N-13-cis-retinoyl cysteic acid 1:1.1:1.1 (w/w/w) | 9 mg/ml NaCl | 34 | $(2.6 \pm 0.15) \times 10^{-9}$ | 4.6[a] | $(6.2 \pm 0.15) \times 10^{-9}$ | 4.4[a] |
| NOVANTRONE ® | 50 mg/ml glucose | — | $(2.1 \pm 0.06) \times 10^{-9}$ | — | $(1.1 \pm 0.02) \times 10^{-9}$ | — |
| Mitoxantrone-Na salt of methyl ester of N-all-trans-retinoyl cysteic acid-Na salt of methyl ester of N-13-cis-retinoyl cysteic acid 1:3.4:3.4 (w/w/w) | 50 mg/ml glucose | — | $(9.0 \pm 0.34) \times 10^{-10}$ | 2.3[b] | $(3.7 \pm 0.09) \times 10^{-10}$ | 3.0[b] |
| HYCAMTIN ® | 9 mg/ml NaCl | — | $(2.6 \pm 0.21) \times 10^{-6}$ | — | $(7.3 \pm 0.33) \times 10^{-7}$ | — |
| Topotecan-Na salt of methyl ester of N-all-trans-retinoyl cysteic acid-Na salt of methyl ester of N-13-cis-retinoyl cysteic acid 1:3.4:3.4 (w/w/w) | 6 mg/ml NaCl, 0.3 mg/ml KCl, calcium chloride hexahydrate 0.4 mg/ml CaCl$_2$ dihydrate, 3.1 mg/ml Na lactate | 14 | $(7.2 \pm 0.22) \times 10^{-7}$ | 3.6[c] | $(1.0 \pm 0.05) \times 10^{-7}$ | 7.3[c] |
| CAMPTO ® | 9 mg/ml NaCl | — | $(2.5 \pm 0.26) \times 10^{-5}$ | — | $(8.5 \pm 0.36) \times 10^{-6}$ | — |
| Irinotecan-Na salt of methyl ester of N-all-trans-retinoyl cysteic acid-Na salt of methyl ester of N-13-cis-retinoyl cysteic acid | 6 mg/ml NaCl, 0.3 mg/ml KCl, calcium chloride hexahydrate 0.4 mg/ml | 12 | $(7.8 \pm 0.53) \times 10^{-6}$ | 3.2[d] | $(6.7 \pm 0.29) \times 10^{-7}$ | 12.7[d] |

TABLE 5-continued

| Formulation | Solvent | Particle size, nm | IC$_{50}$ day 3 | EF day 3 | IC$_{50}$ day4 | EF day 4 |
|---|---|---|---|---|---|---|
| 1:3.4:3.4 (w/w/w) | CaCl$_2$ dihydrate, 3.1 mg/ml Na lactate | | | | | |

Enhancement factors were calculated versus:
[a]ADRIAMYCIN®,
[b]NOVANTRONE®,
[c]HYCAMTIN® and
[d]CAMPTO®.

Example 15

A One Month Toxicity Study of Formulation "Doxorubicin-Sodium Salt of the Methyl Ester of N-all-trans-retinoyl Cysteic Acid-Sodium Salt of the Methyl Ester of N-13-cis-retinoyl Cysteic Acid (w/w/w 1:1.05:1.05)" in Rats The tested formulation was prepared by reconstitution in saline of freeze dried mixture of Doxorubicin-Sodium Salt of the Methyl Ester of N-all-trans-retinoyl Cysteic Acid-Sodium Salt of the Methyl Ester of N-13-cis-retinoyl Cysteic Acid. The experiment was performed in 58 male and 58 female SPF Wistar rats of the strain HanTac:WH (GALAS). The animals were allocated to 4 groups: Group 1 (0.9% saline), Group 2 (Doxorubicin 6 mg/kg), Group 3 (title formulation 4 mg/kg) and Group 4 (title formulation 6 mg/kg). Group 2 receives the same dosage of doxorubicin as Group 4 and acts as a positive control for direct comparison with Group 4. Treatment was performed by intravenous injection once weekly. As severe treatment related clinical signs were seen in Groups 2 and 4 after 3 doses (after dosings on Days 1, 8 and 15) all animals were not dosed on Day 22, but dosing was resumed on Day 29. As resuming, dosing on Day 29 resulted in intolerable clinical signs and as it was judged that several animals would have to be euthanized, the pre-mature termination on Day 33 of Groups 2 and 4 was decided. Groups 1 and 3 received the fifth dose on Day 36 and were terminated on Day 39. Clinical signs, body weight, food consumption, ophtalmoscopic examination, clinical pathology, urinalysis, urine microscopy, readings of the bone marrow, organ weight recordings, macroscopical and microscopical examinations were used as criteria to disclose any adverse side effect. Furthermore, blood samples were collected for toxicokinetic evaluation on Day 1. Intravenous administration of the title formulation at doses of 4 and 6 mg/kg/day once weekly for 5 and 4 repeated doses, respectively, caused severe treatment related findings at the clinical observations, body weight recordings, food consumption recordings, at the haematological and clinical chemistry analysis, at the bone marrow readings, at the organ weight measurements and at the histopathological examinations. Toxicological findings after repeated doses were expected for the tested cytostatic formulations containing Doxorubicin. Several animals were euthanized in each of Group 2, 3 and 4 due to severe treatment related clinical signs. In addition, one animal was found dead in each of Groups 2 and 4. Pronounced lowering in body weight and lower body weight gain were seen in all groups treated with the title formulation and Doxorubicin when compared to the control animals. The toxicity profile of the title formulation was similar to Doxorubicin with exception that signs such as severe itching and scratching around the neck (including self inflicting wounds) were more severe in the positive control Group 2. Also a severe sign of toxicity was fluid-filled abdomens which was only observed in the positive control Group 2. This example demonstrates that nanoparticle formulation "Doxorubicin-Sodium Salt of the Methyl Ester of N-all-trans-retinoyl Cysteic Acid-Sodium Salt of the Methyl Ester of N-13-cis-retinoyl Cysteic Acid (w/w/w 1:1.05:1.05)" has a lower toxicity as compared to identical concentrations of conventional formulation of Doxorubicin.

Although the invention has been described with regard to certain embodiments, including the best mode presently known to the inventors, it should be understood that various changes and modifications as would be obvious to one having the ordinary skill in this art may be made without departing from the scope of the invention as set forth in the claims appended hereto.

The invention claimed is:

1. A drug delivery system for administration of a pharmaceutically active substance that is a cationic amphiphile by itself and has a solubility per se in water of at least 4 mg/ml, wherein the drug delivery system comprises nanoparticles smaller than about 50 nm having a solubility in water below 0.1 mg/ml, said nanoparticles being formed by said substance in association with a sodium salt of the methyl ester of N-all-trans-retinoyl cysteic acid, a sodium salt of methyl ester of N-13-cis-retinoyl cysteic acid, or a combination thereof.

2. A drug delivery system according to claim 1, wherein said nanoparticles have a solubility in water below 0.01 mg/ml.

3. A drug delivery system according to claim 1, wherein said substance is non-covalently associated with a sodium salt of the methyl ester of N-all-trans-retinoyl cysteic acid, a sodium salt of methyl ester of N-13-cis-retinoyl cysteic acid, or a combination thereof.

4. A drug delivery system according to claim 1, wherein said substance is a cytotoxic or a cytostatic compound.

5. A drug delivery system according to claim 1, wherein said substance is a cytotoxic or cytostatic compound chosen among a protonated form of doxorubicin, mitoxantrone, epirubicin, daunorubicin, idarubicin, topotecan, irinotecan, vinblastine, vincristine, vinorelbine, amsacrine, procarbazine, mechlorethamine, or a combination thereof.

6. A drug delivery system according to claim 4 for use in treatment of cancer.

7. A pharmaceutical composition comprising a pharmaceutically acceptable carrier and the drug delivery system according to claim 1.

8. A pharmaceutical composition according to claim 7 in the form of an aqueous solution, a gel, a cream, an ointment, a tablet, a capsule, or a softgel.

9. A method for the preparation of a drug delivery system for administration of at least one pharmaceutically active substance that is a cationic amphiphile by itself and has a solubility per se in water of at least 4 mg/ml, wherein said substance is combined with a sodium salt of the methyl ester of N-all-trans-retinoyl cysteic acid, a sodium salt of methyl ester of N-13-cis-retinoyl cysteic acid, or a combination thereof to form nanoparticles smaller than about 50 nm having a solubility in water below 0.1 mg/ml.

10. A method according to claim 9, wherein a sodium salt of the methyl ester of N-all-trans-retinoyl cysteic acid, a sodium salt of methyl ester of N-13-cis-retinoyl cysteic acid, or a combination thereof is non-covalently bound to said substance.

11. A method according to claim 9, wherein said nanoparticles have a solubility in water below 0.01 mg/ml.

12. A method for the preparation of pharmaceutical composition comprising a pharmaceutically acceptable carrier and a drug delivery system according to claim 1, wherein said drug delivery system is combined with an amount of about 0.2-10 equivalents, based on the cationic charge of the amphiphile comprised in the drug delivery system, of the methyl ester of N-all-trans-retinoyl cysteic acid, a sodium salt of methyl ester of N-13-cis-retinoyl cysteic acid, or a combination thereof.

13. A method for enhancing the drug efficiency of at least one pharmaceutically active substance that is a cationic amphiphile by itself and has a solubility per se in water of at least 4 mg/ml, wherein said substance is combined with a sodium salt of the methyl ester of N-all-trans-retinoyl cysteic acid, a sodium salt of methyl ester of N-13-cis-retinoyl cysteic acid, or a combination thereof to form nanoparticles having a solubility in water below 0.1 mg/ml.

14. A method according to claim 13, wherein a sodium salt of the methyl ester of N-all-trans-retinoyl cysteic acid, a sodium salt of the methyl ester of N-13-cis-retinoyl cysteic acid, or a combination thereof is non-covalently bound to said substance.

15. A method according to claim 13, wherein said substance is combined with an excess of about 0.2-10 equivalents of said sodium salt of the methyl ester of N-all-trans-retinoyl cysteic acid, sodium salt of methyl ester of N-13-cis-retinoyl cysteic acid, or combination thereof.

16. A method according to claim 13, wherein said nanoparticles have a solubility in water below 0.01 mg/ml.

17. A method for increasing the bioavailability of at least one pharmaceutically active substance that is a cationic amphiphile by itself and has a solubility per se in water of at least 4 mg/ml,
wherein said substance is combined with a sodium salt of the methyl ester of N-all-trans-retinoyl cysteic acid, a sodium salt of the methyl ester of N-13-cis-retinoyl cysteic acid, or a combination thereof to form nanoparticles having a solubility in water below 0.1 mg/ml.

18. A method according to claim 17, wherein a sodium salt of the methyl ester of N-all-trans-retinoyl cysteic acid, a sodium salt of the methyl ester of N-13-cis-retinoyl cysteic acid, or a combination thereof is non-covalently bound to said substance.

19. A method according to claim 17, wherein said substance is combined with an excess of about 0.2-10 equivalents of said sodium salt of the methyl ester of N-all-trans-retinoyl cysteic acid, sodium salt of methyl ester of N-13-cis-retinoyl cysteic acid, or combination thereof.

20. A method according to claim 17, wherein said nanoparticles have a solubility in water below 0.01 mg/ml.

21. A method for the treatment of cancer, wherein a drug delivery system according to claim 1 is administered in a therapeutically effective amount to a patient in need of such treatment.

22. A method for the treatment of cancer, wherein a pharmaceutical composition according to claim 7 in the form of an aqueous solution, a gel, a cream, an ointment, a tablet, a capsule, or a softgel, is administered in a therapeutically effective amount to a patient in need of such treatment.

* * * * *